United States Patent [19]

Homan et al.

[11] Patent Number: 4,880,702
[45] Date of Patent: Nov. 14, 1989

[54] THREE LAYER COMPOSITION FOR STABLIZING A DENTURE

[75] Inventors: Morio Homan, Sakai; Nizo Sugie, Hachiouji; Masakiyo Yoshimura, Kawachinagano; Yoshikazu Shirakawa, Yamatokooriyama, all of Japan

[73] Assignee: Shionogi & Co., Ltd., Osaka, Japan

[21] Appl. No.: 136,633

[22] Filed: Dec. 22, 1987

[30] Foreign Application Priority Data

Dec. 26, 1986 [JP] Japan ................... 61-311088

[51] Int. Cl.⁴ ................ C09J 7/00; A61C 13/23; A61K 6/00
[52] U.S. Cl. ................... 428/354; 106/35; 156/326; 156/327; 156/328; 156/336; 428/355; 428/484; 428/523; 433/168.1; 433/180; 523/120
[58] Field of Search .............. 523/115, 118, 120; 428/484, 523, 354, 355; 156/326, 327, 328, 336; 433/168.1, 180; 106/35

[56] References Cited

U.S. PATENT DOCUMENTS

| | | | |
|---|---|---|---|
| 2,978,812 | 4/1961 | Rosenthal et al. | 433/199.1 |
| 3,990,149 | 11/1976 | Nedwig | 433/180 |
| 4,202,098 | 5/1980 | Russo | 433/168.1 |
| 4,280,936 | 7/1981 | Dhabhar et al. | 156/328 |
| 4,373,036 | 2/1983 | Chang et al. | 523/120 |
| 4,518,721 | 5/1985 | Dhabhar et al. | 433/180 |
| 4,522,956 | 6/1985 | Dhabhar et al. | 523/120 |
| 4,529,748 | 7/1985 | Wienecke | 523/120 |
| 4,530,942 | 7/1985 | Dhabhar et al. | 523/120 |
| 4,569,955 | 2/1986 | Dhabhar | 523/120 |
| 4,632,880 | 12/1986 | Lapidus | 428/523 |

FOREIGN PATENT DOCUMENTS 0224767  7/1985  German Democratic Rep. ................ 433/180

*Primary Examiner*—Paul Lieberman
*Assistant Examiner*—Linda D. Skaling
*Attorney, Agent, or Firm*—Wenderoth, Lind & Ponack

[57] ABSTRACT

A composition for stabilizing a denture in the form of a thin strip consisting of three layers, piled up one over another, which composition is characterized in that:
  (a) a swelling ability and solubility of outside layers are higher than those of an inside layer,
  (b) the swelled outside layers have an ability to adhere to gums and a denture base,
  (c) the inside layer has a self-supporting ability and a shape-retaining ability for the outside layers, and
  (d) the inside layer has an ability to adhere to the gums and the denture base after the outside layers have flowed away through dissolution.

10 Claims, No Drawings

THREE LAYER COMPOSITION FOR STABLIZING A DENTURE

The present invention relates to a novel adhesive-type composition for stabilizing a denture, which is easy to apply to the denture, has a prolonged denture-retention time, and gives a superior touch-feeling.

Inadaptation of a denture will occur with the lapse of time due to the thinning of gums, even if the denture is elaborately prepared so that it may precisely fit the gums, and therefore, insufficient mastication of food and/or difficulty of speaking are often caused by such inadaptation. In such case, readjustment of the denture by a dentist becomes necessary. However, immediate readjustment is often difficult due to various reasons, such as economic or time limitation. Accordingly, a stabilizer for a denture is employed as a temporary adjustment for the inadaptation until the readjustment by a dentist is performed.

Commercial adhesive-type stabilizers for a denture now available includes a powdery composition of water-soluble natural polymer, semisynthetic polymer or synthetic polymer, as well as a creamy composition containing the above water-soluble polymer and a high viscous liquid, such as vaseline. However, the use of these powdery and creamy stabilizers is accompanied by some difficulty because it is not easy to determine the suitable amount to be used. In addition, these known stabilizers possess the following drawbacks: the powdery stabilizer confers an unpleasant feeling of stickiness on an oral cavity because the powder tends to stick to a portion other than the intended portion, while the creamy stabilizer has a shortened denture-retention time due to the high resolving property in saliva and gives an unpleasant feeling of stickiness on an oral cavity due to the insoluble vaseline left in the cavity.

BRIEF DESCRIPTION OF THE INVENTION

The present inventors have made an intensive study for the purpose of developing an adhesive-type composition for stabilizing a denture, which is free from the above drawbacks, i.e., a novel composition which is easy to apply to a denture and capable of efficiently stabilizing a denture for a long time and minimizing an unpleasant feeling suffered by a user, and have found that the above purpose was accomplished by providing a novel fixed-type and adhesive-type composition, which essentially consists of three layers. Each of the outside layers of the stabilizing composition of the invention consists of the first composition which readily adheres to gums and a denture base after contact with water or saliva, and the inside layer consists of the second composition capable of supporting and retaining the outside layers, and also capable of adhering to the gums and the denture base after the outside layers have flowed away through dissolution.

Thus, the present invention provides a composition for stabilizing a denture in the form of a thin strip consisting of three layers, piled up one over another, which composition is characterized in that:

(a) a swelling ability and solubility of outside layers are higher than those of an inside layer, (b) the swelled outside layers have an ability to adhere to gums and a denture base, (c) the inside layer has a self-supporting ability and a shape-retaining ability for the outside layers, and (d) the inside layer has an ability to adhere to the gums and the denture base after the outside layers have flowed away through dissolution.

DETAILED DESCRIPTION OF THE INVENTION

Each of the outside layers of the composition of the present invention consists of a polymer capable of adhering to gums and a denture base after contact with water or saliva, such as polyethylene oxide (average molecular weight of about 200,000 to 10,000,000), sodium carboxymethyl cellulose or polyvinyl alcohol. The above polymer may be used either alone or in admixture with one or more of the designated polymers. A mixture of two or more homologous polymers which differ one another only in their molecular weights may also be employed. If sodium carboxymethyl cellulose is used, its content should be less than 20% by weight of the total weight of the present composition for securing the safety and molding property of the composition.

The inside layer of the composition according to the present invention consists of microcrystalline wax and the above mentioned polymer or polymers used for the outside layers. The use of microcrystalline wax confers a self-supporting ability on the inside layer and allows the retarded swelling and dissolving of the inside layer. The average molecular weight of polyethylene oxide used for the preparation of the inside layer is preferably about 2,000,000 to 10,000,000, more preferably about 3,000,000 to 5,000,000. The preferable inside layer contains about 35 to 65% by weight of polyethylene oxide, about 5 to 20% by weight of sodium carboxymethyl cellulose, and about 20 to 40% by weight of microcrystalline wax.

The outside layers and the inside layer of the composition of the invention may optionally contain additional component or components, such as a plasticizer (e.g. polybutene or sucrose fatty acid ester), a coloring agent (e.g. a dye or a pigment), a flavouring agent or a bactericidal agent, in an amount which causes no adverse effect on the desired properties of the present composition.

The composition of the present invention can be prepared, for example, in the following manner. Thus, the component or components for the outside layers are mixed if necessary, kneaded and rolled by a standard procedure, which gives a film of about 0.03 to 0.2 mm, preferably about 0.04 to 0.1 mm, in thickness. Subsequently, the components for the inside layer are kneaded by a conventional procedure and molded to a film of about 0.2 to 0.8 mm in thickness. Two sheets of the film prepared for the outside layers are laminated on the front and reverse sides of the film prepared for the inside layer by a pressure adhesion, which gives the present stabilizing composition. The thickness and the width of the composition are preferably about 0.3 to 1.0 mm and about 3 to 10 mm, respectively, which provides a suitable retention time of the composition, a desired expansion of the composition in a pocket between a denture base and gums, and a minimum amount of superfluous composition pushed out of the pocket. On the other hand, the length of the present composition is not critical because the composition can be cut to strips so as to adapt to any particular denture before use.

The composition of the present invention thus obtained can be easily set to a denture in a suitable amount because it has a fixed shape. The composition can also be employed without superfluousness and without insufficiency. The composition is also free from an unpleasant feeling of stickiness caused by excessive composition pushed out of the pocket and can fix and retain a denture for a long time.

The present invention is illustrated by the following Examples, but should not be construed to be limited thereto.

EXAMPLE 1

Polyethylene oxide (average molecular weight of 4,000,000) (12.5 kg), sodium carboxymethyl cellulose (trade name: SELLOGEN F-3H) (1.5 kg) and polybutene (average degree of polymerization: 2,300) (1.0 kg) were mixed together for three minutes using a supermixer, kneaded at 50° C. using a continuous kneader, and rolled using a L type calendar to obtain a film of 0.07 mm in thickness.

Subsequently, polyethylene oxide (average molecular weight of 4,000,000) (7.0 kg), microcrystalline wax (4.5 kg), sodium carboxymethyl cellulose (1.5 kg), and polybutene (average degree of polymerization: 2,300) (2.0 kg) were kneaded at 30° C. for 60 minutes using a planetary mixer, and then extruded to give a film of 0.6 mm in thickness.

On the front and reverse sides of the film obtained in the above second step, two sheets of the film prepared in the first step were laminated by a pressure adhesion to give a bonded laminate of 0.6 mm in thickness, which was in turn cut into strips of 6 mm in width and 50 mm in length.

A setting of this strip on a complete denture, which had lost compatibility with gums, recovered high compatibility and allowed excellent denture-retention for a long time.

EXAMPLE 2

Polyethylene oxide (average molecular weight of 400,000) (4 kg), polyethylene oxide (average molecular weight of 5,000,000) (8 kg) sodium carboxymethyl cellulose (SELLOGEN F-3H) (1.5 kg), and polybutene (1.5 kg) were mixed at 30° C. for 10 minutes using a supermixer, kneaded at 50° C. using a continuous kneader, and rolled using a L type calendar to obtain a film of 0.1 mm in thickness. Subsequently, polyethylene oxide (average molecular weight of 5,000,000) (7.1 kg), microcrystalline wax (4.3 kg), sodium carboxymethyl cellulose (1.5 kg), polybutene (average degree of polymerization: 2,300) (2.2 kg), and a suitable amount of a coloring agent and a flavouring agent were kneaded at 30° C. for 45 minutes using a planetary mixer, and extruded to give a film of 0.4 mm in thickness.

On the front and reverse sides of the film obtained in the last step, two sheets of the film prepared in the first step were laminated to give a bonded laminate of 0.6 mm in thickness, which was in turn cut into strips of 5 mm in width and 40 mm in length.

A setting of this strip on a denture having a decreased compatibility with gums resulted in an increase of types of foods which can be chewed (e.g. a rice cake or a rice cracker) and allowed excellent denture retention for a long time.

EXAMPLE 3

Polyethylene oxide (average molecular weight of 4,000,000) (7 kg), sodium carboxymethyl cellulose (1.5 kg), microcrystalline wax (4.1 kg), and sucrose fatty acid ester (2 kg) were kneaded at 30° C. for 50 minutes using a planetary mixer, and then molded using a extrusion machine to give a film of 0.5 mm in thickness. On the front and reverse sides of the inside layer thus obtained, polyvinyl alcohol films of 0.05 mm in thickness, which had been prepared by conventional casting procedure, were laminated, and the resulting laminate was cut into strips of 7 mm in width and 45 mm in length.

Application of this strip to a denture, which had generated unpleasant sounds at a time of speaking as a result of a decreased compatibility with gums, led to an elimination of such unpleasant sounds, and this effect continued for a long time.

What is claimed is:

1. A composition for stabilizing a denture in the form of the thin strip consisting of three layers, piled up one over another, which composition consists essentially of:
   (a) two outside layers which consist essentially of a polymer in an amount sufficient to adhere each of said outside layers to gums and a denture base after contact with water or saliva, said polymer being selected from the group consisting of polyethylene oxide having an average molecular weight of about 200,000 to 10,000,000, sodium carboxymethyl cellulose and polyvinyl alcohol and mixtures of these polymers, provided that if sodium carboxymethyl cellulose is used, its content should be less than 20% by weight of the total weight of the present composition; and
   (b) an inside layer which consists essentially of microcrystalline wax in an amount sufficient to impart a self-supporting ability and to retard swelling and dissolution of said inside layer and a polymer in an amount sufficient to adhere said inside layer to gums and a denture base, after contact with water or saliva when said outside layers have been dissolved, said polymer being selected from the group consisting of polyethylene oxide having an average molecular weight of about 2,000,000 to 10,000,000, sodium carboxymethyl cellulose and polyvinyl alcohol and mixtures of these polymers;
      (i) said outside layers having a thickness of about 0.03 to 0.2 mm and said inside layer having a thickness of about 0.2 to 0.8 mm;
      (ii) said film strip having a thickness of about 0.3 to 1.0 mm and width of about 3 to 10 mm;
      (iii) the swelling ability and solubility of said outside layers being higher than those of said inside layer;
      (iv) the swelled outside layers having an ability to adhere to gums and a denture base;
      (v) said inside layer having a self-supporting ability and a shape-retaining ability for said outside layers; and
      (vi) said inside layer having an ability to adhere to the gums and the denture base after said outside layers have dissolved.

2. The composition according to claim 1, wherein the outside layers consist essentially of polyethylene oxide having an average molecular weight of about 200,000 to 10,000,000 and sodium carboxymethyl cellulose.

3. The composition according to claim 1, wherein the outside layers consist essentially of polyvinyl alcohol.

4. The composition according to claim 1, wherein the outside layers further contain a polymeric plasticizer selected from the group consisting of polybutene and a sucrose fatty acid ester.

5. The composition according to claim 4, wherein the outside layers additionally contain a coloring agent, a flavouring agent, a bactericidal agent, or mixtures thereof.

6. The composition according to claim 1, wherein the inside layer consists essentially of polyethylene oxide having an average molecular weight of about 2,000,000 to 10,000,000, sodium carboxymethyl cellulose and microcrystalline wax.

7. The composition according to claim 1, wherein the inside layer essentially consists of about 35 to 65% by weight of polyethylene oxide, about 5 to 20% by weight of sodium carboxymethyl cellulose, and about 20 to 40% by weight of microcrystalline wax.

8. The composition according to claim 1, wherein the inside layer further contains a polymeric plasticizer selected from the group consisting of polybutene and sucrose fatty acid ester.

9. The composition according to claim 8, wherein the inside layer additionally contains a coloring agent, a flavouring agent, a bactericidal agent, or mixtures thereof.

10. The composition according to claim 1, wherein the thickness of the outside layer is about 0.04 to 0.1 mm.

* * * * *

UNITED STATES PATENT AND TRADEMARK OFFICE
CERTIFICATE OF CORRECTION

PATENT NO. : 4,880,702

DATED : November 14 1989

INVENTOR(S) : Morio HOMAN, Nizo SUGIE, Masakiyo YOSHIMURA and Yoshikazu SHIRAKAWA It is certified that error appears in the above-identified patent and that said Letters Patent is hereby corrected as shown below:

First page (title page), first column, line designated "[73] Assignee:" after "Japan", insert -- and Kyowa Limited, Osaka, Japan --.

Signed and Sealed this

Sixteenth Day of April, 1991

Attest:

HARRY F. MANBECK, JR.

*Attesting Officer*  *Commissioner of Patents and Trademarks*